(12) United States Patent
Cichocki et al.

(10) Patent No.: US 8,883,245 B2
(45) Date of Patent: Nov. 11, 2014

(54) METHOD OF COATING SURGICAL NEEDLES

(71) Applicant: Ethicon, Inc., Somerville, NJ (US)

(72) Inventors: Frank Cichocki, Easton, PA (US); Duan Li Ou, Warren, NJ (US); Brian Blasic, Flemington, NJ (US)

(73) Assignee: Ethicon, Inc., Somerville, NJ (US)

(*) Notice: Subject to any disclaimer, the term of this patent is extended or adjusted under 35 U.S.C. 154(b) by 0 days.

(21) Appl. No.: 13/800,181

(22) Filed: Mar. 13, 2013

(65) Prior Publication Data
US 2014/0277120 A1 Sep. 18, 2014

(51) Int. Cl.
*A61B 17/34* (2006.01)
*B05D 3/04* (2006.01)
*A61M 3/00* (2006.01)
*A61B 17/06* (2006.01)

(52) U.S. Cl.
CPC .............................. *A61B 17/06066* (2013.01)
USPC ........................... 427/2.28; 427/348; 606/185

(58) Field of Classification Search
USPC .................................. 427/348, 2.28; 606/185
See application file for complete search history.

(56) References Cited

U.S. PATENT DOCUMENTS

| | | |
|---|---|---|
| 5,181,416 A | 1/1993 | Evans |
| 5,213,839 A * | 5/1993 | Awazu et al. ............... 427/2.28 |
| 5,630,268 A | 5/1997 | Smith |
| 5,644,834 A | 7/1997 | Smith |
| 5,661,893 A | 9/1997 | Smith |
| 5,701,656 A | 12/1997 | Smith |
| 5,776,268 A | 7/1998 | McJames |
| 5,913,875 A | 6/1999 | Smith |
| 6,018,860 A | 2/2000 | Smith |
| 6,252,195 B1 | 6/2001 | Mosavi |
| 6,652,562 B2 | 11/2003 | Collier |
| 6,997,815 B2 | 2/2006 | Devine |
| 7,041,088 B2 | 5/2006 | Nawrocki |
| 2011/0111116 A1* | 5/2011 | Maurer et al. ............... 427/2.28 |
| 2011/0112565 A1 | 5/2011 | Maurer |
| 2011/0112566 A1 | 5/2011 | Maurer |
| 2011/0152926 A1 | 6/2011 | Vetrecin |
| 2012/0321776 A1 | 12/2012 | Vetrecin |

* cited by examiner

*Primary Examiner* — Cachet Sellman
(74) *Attorney, Agent, or Firm* — E. Richard Skula

(57) ABSTRACT

A novel silicone coating process for surgical needles is disclosed. Coating solutions are applied to a surgical needle and a stream of air is directed at the needle in a direction substantially parallel to the central longitudinal axis of the distal section of the needle, providing superior coatings and performance.

20 Claims, 9 Drawing Sheets

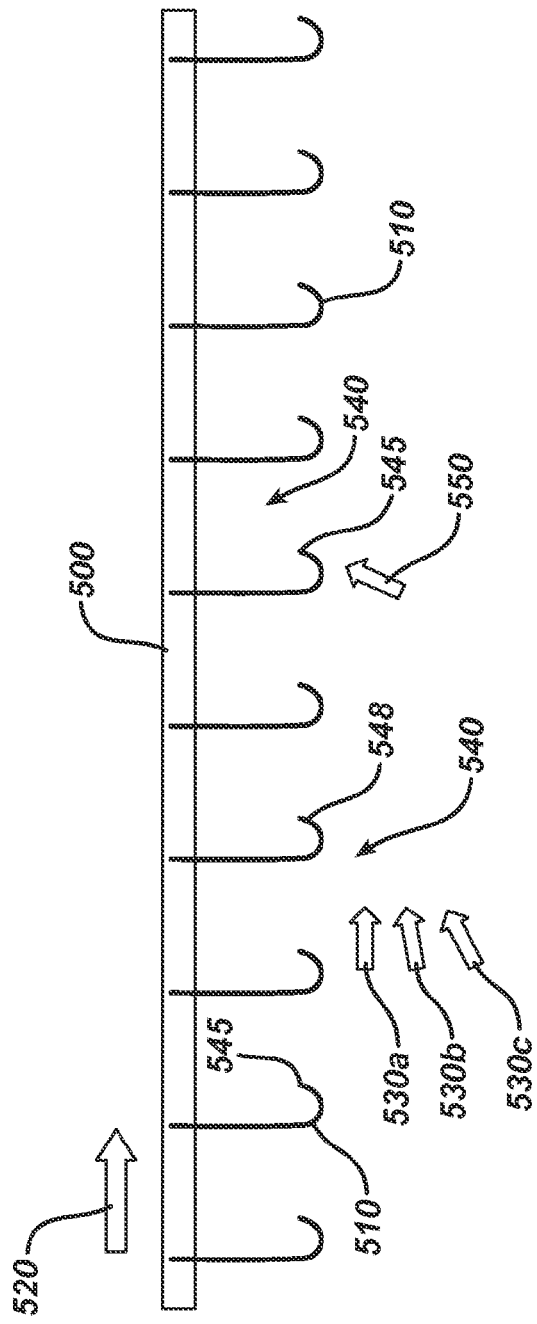

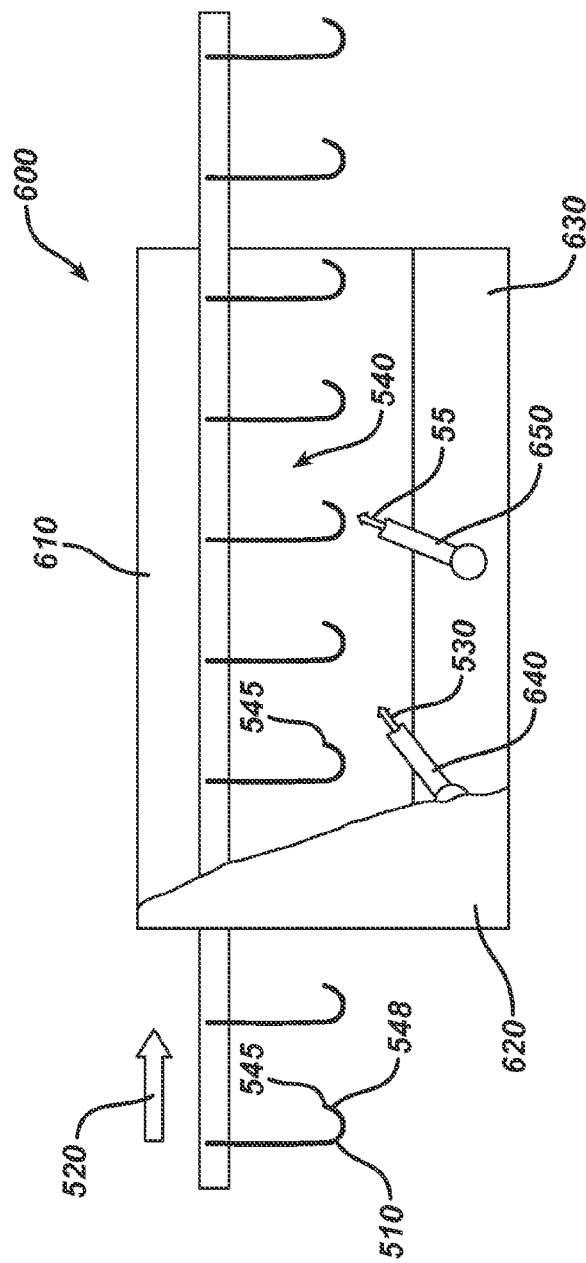

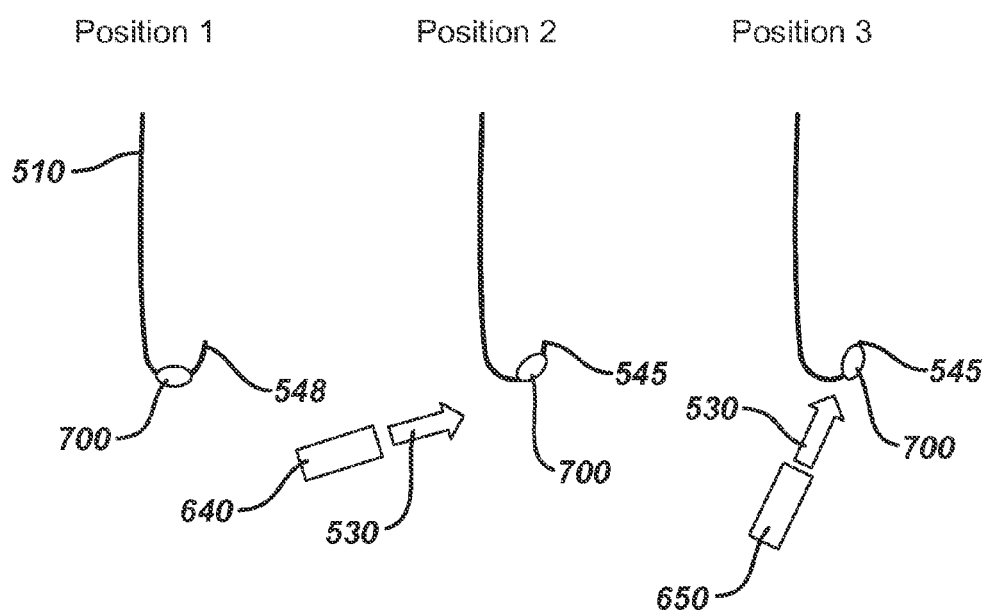

120x160μm

METHOD OF COATING SURGICAL NEEDLES

TECHNICAL FIELD

The field of art to which this invention relates is surgical needles, more specifically, methods of coating surgical needles with lubricious coatings.

BACKGROUND OF THE INVENTION

Surgical needles and attached surgical sutures are widely used medical devices in the medical arts. Surgical sutures are used in most surgical procedures for a variety of functions including tissue repair and approximation, securement of medical devices to tissue including mesh implants, artificial heart valves, etc., and vessel anastomosis and attachment, bone repair, tissue anchoring, etc. In order to have maximum utility to the surgeon during a surgical procedure, it is necessary that the surgical needle have the capability of easily and smoothly penetrating and moving through tissue for multiple passes with minimal force. The amount of force necessary to move a surgical needle through tissue with minimal trauma to the tissue will depend in part on the type of tissue to be penetrated. Various needle designs are available for use with different types of tissue to provide the desired tissue penetration including taper point needles, blunt tip needles, and cutting edge needles. The wire size of the needle will also affect the force to penetrate. In addition, it is known to apply lubricious coatings to surgical needles to improve their penetration and movement through tissue. Lubricious coatings are typically required for implantable or insertable medical devices such as hypodermic needles, surgical needles, and cutting equipment with cutting edges such as knives, scalpels, scissors and blades with cutting edges that contact tissue. The primary purpose of such coatings is to reduce the penetration force and ease the insertion of the device into tissue.

Most conventional lubricious coatings are silicone polymer based. Examples of such silicone materials include the polyalkylsiloxanes. The preferred polyalkylsiloxanes conventionally used are polydimethylsiloxanes. The lubricious silicone coatings may be applied to surgical needles using conventional coating processes known in this art, including dip coating and spraying. Examples of silicone coating compositions and coating processes are contained in the following patent applications which are incorporated by reference: U.S. patent application Ser. Nos. 12/858,489; 12/858,485; 12/858,481; 10/034,636; 10/678,560 (U.S. Pat. No. 7,041,088); Ser. No. 13/162,837 and Ser. No. 12/642,373.

Surgical needles are commonly manufactured using high speed production processes. The production processes typically utilize high speed inline manufacturing lines. Surgical needle blanks are typically mounted to metal carrier strips and moved through the various manufacturing operations, where they are formed in a step-wise process into surgical needles. The manufacturing process steps may include needle point formation, bending, heat treatment, and borehole drilling. In addition, the finished needles may be coated with silicone coatings, e.g., dip coated in silicone coating baths, and moved to drying and curing ovens while on the metal carrier strips. Examples of high speed needle manufacturing processes and equipment are disclosed in the following patents which are incorporated by reference: U.S. Pat. Nos. 5,630,268, 5,644,834, 5,661,893, 5,701,656, 5,776,268, 5,913,875, 6,018,860, and 6,252,195.

Lubricious coatings on most surgical needles are typically applied by conventional dip coating processes, in which the needles are first immersed into a silicone solution, and then drained and exposed to a thermal cycle to remove the solvent and cure the silicone polymer. Other conventional coating processes such as spraying or brushing are also utilized. In a high speed automated production system, surgical needles are coated while mounted to a carrier strip in a semi-continuous manner when employing a dip coating process, wherein a section of the strip is immersed in a tank of the coating solution and then moved out to a blow off device that is used on-line to remove the excess silicone solution prior to a thermal curing step. Although such conventional coating processes are typically effective for their intended purpose, and produce coatings on surgical needles that comply with requirements, there may be some deficiencies associated with conventional dip coating processes using conventional lubricious coatings. Conventional silicone coatings have substantially long cure times and coated needles must be moved to a curing oven while the coating is still wet. The wet coating is susceptible to damage and to being contaminated by dust and dirt particles in the environment, potentially compromising the integrity and performance of the coating. In addition, the wet coatings have a tendency to wick, shrink or move away from the distal end and distal piercing point of the needle, potentially reducing the thickness of the coating to unacceptably low levels and possibly affecting penetration performance.

Accordingly, there is a need in this art for novel coating processes for coating surgical needles with lubricious coatings that provide for improved coating application and coating characteristics.

SUMMARY OF THE INVENTION

A novel coating process for applying a silicone coating to surgical needles is disclosed. In the novel process of the present invention, a silicone coating is applied to a surgical needle having a longitudinal central axis and a distal tip section wherein the needle is mounted to a carrier strip. The surgical needle is dipped into a silicone coating solution by moving the needle into a silicone coating solution bath, wherein the needle is mounted to the strip such that the distal tip section of the needle is pointing upwardly. The needle is then moved out of the coating bath. A stream of air is directed at the needle along a path that is in a direction substantially parallel to the longitudinal central axis of the distal tip section of the needle, such that a sufficient amount of silicone coating solution is retained on the on the distal tip section. Then the silicone coating on the needle is cured. The needles may be optionally mounted to a carrier other than a carrier strip.

Another aspect of the present invention is a novel coating process for applying a silicone coating to surgical needles is disclosed. In the novel process, a silicone coating is applied to a surgical needle having a longitudinal central axis and a distal tip section wherein the needle is mounted to a carrier strip. The silicone coating is applied to the needle by a coating process, wherein the needle is mounted to the strip such that the distal tip section of the needle is pointing upwardly. The needle is then moved to a stream of air that is directed at the needle along a path that is in a direction substantially parallel to the longitudinal central axis of the distal tip section of the needle, such that a sufficient amount of silicone coating solution is retained on the tip section. Then, the silicone coating on the needle is cured. The needles may be optionally mounted to a carrier other than a carrier strip.

Yet another aspect of the present invention is a surgical needle having a silicone coating, wherein the coating is applied by a novel coating process of the present invention, such as those coating processes described above.

The novel coating processes of the present invention provide for surgical needles having improved silicone coatings, wherein the coatings have improved characteristics and performance along with increased silicone coating at the distal tip section of the needles.

These and other aspects and advantages of the present invention will become more apparent from the following description and accompanying drawings.

BRIEF DESCRIPTION OF THE DRAWINGS

FIGS. 3A-E are schematic views illustrating aspects of the method of the present invention when used in a high speed needle manufacturing operation.

DETAILED DESCRIPTION OF THE INVENTION

Figure 1:
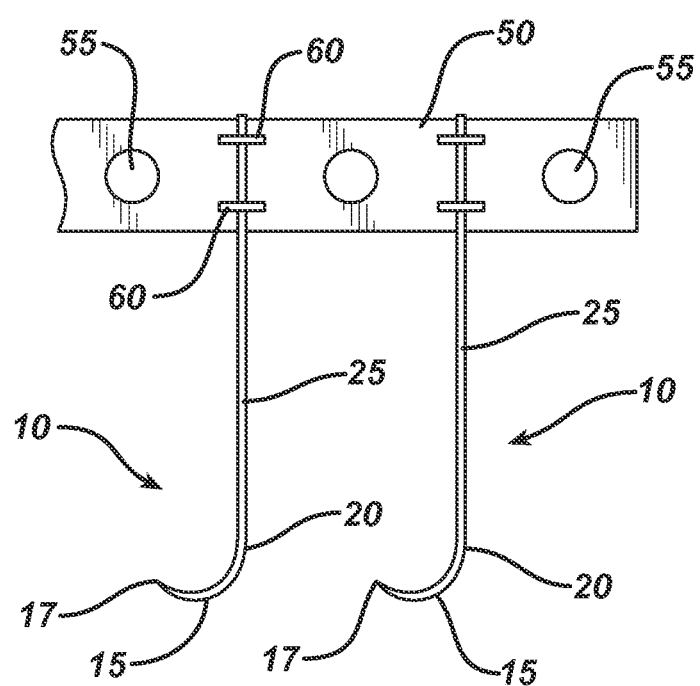
FIG. 1 is a schematic illustrating surgical needles mounted to a carrier strip.

The terms silicone and siloxane are conventionally used interchangeably in this art, and that usage has been adopted herein.

The present invention is directed to novel processes for applying lubricious silicone coating compositions, which are particularly useful for coating surfaces of medical devices, such as surgical needles and other tissue piercing or cutting devices. The coating compositions include a mixture of a cross-linkable siloxane polymer and a non-cross-linkable siloxane polymer, a conventional silicone cross-linking agent, and a platinum catalyst. The silicone polymer components are blended with conventional aromatic organic solvents, including, for example, xylene and aliphatic organic solvents (such as, for example, hexane or its commercial derivatives) to form coating solutions or compositions. Particularly preferred coating compositions useful in the novel processes of the present invention are disclosed in copending, commonly-assigned U.S. patent application Ser. No. 13/296,771 which is incorporated by reference.

The cross-linkable siloxane polymers useful in the coating compositions useful in the processes of the present invention will have reactive functionalities or terminal functional groups, including but not limited to vinyl-terminated, hydroxyl and acrylate functional groups. An example of a hydroxyl functional, cross-linkable siloxane polymer is hydroxyl terminated polydimethylsiloxane, supplied by Nusil Technology, Caprenteria, Calif. under the trade name of MED4162. The cross-linkable siloxane polymers that can be used in the lubricious coatings of the present invention preferably include vinyl-terminated polydialkylsiloxane or vinyl-terminated polyalkoarylsiloxane. Examples include, but are not limited to, the following vinyl-terminated siloxane polymers: polydimethyl siloxane, polydiphenylsilane-dimethylsiloxane copolymer, polyphenylmethylsiloxane, polyfluoropropylmethyl-dimethylsiloxane copolymer and polydiethylsiloxane. It is particularly preferred to use vinyl-terminated cross-linkable polymethyl siloxane.

The non-cross-linkable siloxanes that can be used in the practice of the present invention include polydimethyl siloxane, polyalkylmethylsiloxane, such as polydiethylsiloxane, polyfluoropropylmethylsiloxane, polyoctylmethylsiloxane, polytetradecylmethylsiloxane, polyoctadecylmethylsiloxane, and polyalkylmethyl dimethylsiloxane, such as polyhexadecymethylsiloxane-dimethyl siloxane. It is particularly preferred to use non-cross-linkable polymethylsiloxanes with weight average molecular weights (Mw) greater than 200,000, preferably about 200,000 to about 1,000,000, which are in the form of non-flowable gum having a viscosity greater than 600,000 cps.

The cross-linking agents that can be used in coatings applied by the novel processes of the present invention include conventional silicone cross-linking agents such as, for example, polymethylhydrosiloxane, polymethylhydro-co-polydimethylsiloxane, polyethyhydrosiloxane, polymethylhydrosiloxane-co-octylmethylsiloxane, polymethylhydrosiloxane-co-methylphenylsiloxane. One preferred conventional cross-linking agent for use in the coatings applied by the novel processes of the present invention is polymethylhydrosiloxane. Precise control of cross-link density in the coatings of the present invention is achieved by precise control of the ratio of non-cross-linkable silicone polymer (e.g., polydimethylsiloxane) to fully cross-linked polymer. The fully cross-linked polymer is formed by a reaction between the functionalized cross-linkable polymer and the cross-linking agent, for example, a vinylsilylation reaction between vinyl-terminated polydimethylsiloxane and polymethylhydrosiloxane optionally in the presence of a platinum complex catalyst. The ratio between non-cross-linkable polymer, e.g., polydimethylsiloxane, and fully cross-linked polymer is sufficiently effective to provide structural reinforcement to the resulting interpenetrating polymer networks, and is typically between about 0.1 wt./wt. and about 9 wt./wt., preferably between about 0.43 wt./wt. and about 2.33 wt./wt. The vinyl-terminated cross-linkable base polymer, e.g., polydimethylsiloxane base polymer, useful in the coatings applied by the processes of the present invention will typically have a weight average molecular weight (Mw) of between about 10,000 and about 500,000 and preferably between about 50,000 to about 250,000. Examples of such a polymer include, but are not limited to: Gelest Product Code No. DMS-V51, DMS-V52, DMS-V61, DMS-V71, etc., available from Gelest, Inc., Morrisville, Pa. 19067.

The cross-linkable siloxane polymer is believed to form the matrix phase of the coating on a surface or surfaces of a medical device. Vinyl-terminated polydimethylsiloxane reacts with polymethylhydrosiloxane cross-linker in the presence of platinum catalyst under appropriate conditions; the vinyl-terminated polydimethylsiloxane linear polymers are fully cross-linked to each other as the result of this reaction. The amount of polymethylhydrosiloxane cross-linker is in large stoichiometric excess compared to the vinyl-terminated polydimethylsiloxane base polymer. It is believed that the extra SiH functional groups in the cross-linker react with the OH functional groups on the surface of the oxide layer of the medical devices, e.g., stainless steel needles, to form Si—O—Fe bonds at elevated temperature. Covalent bonds thus created between the silicone coating and the device or needle surface, as the result of this reaction, result in the adhesive attachment of the coating to the metallic surface. Attachment to a polymeric surface is believed to occur in the following manner: the OH and COOH functions on the surface of a polymeric surface react with SiH functions in the silicone coating to from Si—O—C bonds at elevated temperature.

The polymethyhydrosiloxane cross-linkers, or cross-linking agents, used in the practice of the present invention will typically have a weight average molecular weight (Mw) between about 1000 and about 3000, and preferably between about 1400 and about 2100. An example of this polymer cross-linker includes, but is not limited to, Gelest Product Code No. HMS-991, HMS-992, available from Gelest, Inc., Morrisville, Pa. 19607.

Polymethylhydro-co-polydimethylsiloxane can also be used as cross-linker or cross-linking agent in the coatings applied by the novel processes of the present invention. Examples of this polymer include, but are not limited to, Gelest Product Code No. HMS-301, HMS-501. The weight average molecular weight of such siloxane polymer cross-linking agents will typically be between about 900 and about 5,000, and preferably about 1,200 to about 3,000.

The non-cross-linkable siloxane polymer that may be used in the lubricious coatings applied by the processes of the present invention is preferably trimethylsilyl-terminated polydimethylsiloxane; which is a linear high molecular weight polydimethylsiloxane polymer, and which does not contain reactive functional groups. This polymer provides a non-cross-linked phase in the resulting silicone coating, and is believed to disperse in the matrix phase made from the cross-linked cross-linkable siloxane. The weight average molecular weight of non-cross-linkable siloxane polymer will typically be greater than about 200,000, preferably between about 200,000 to about 10,000,000, and more preferably between about 400,000 to about 700,000. Examples of this polymer include, but are not limited to, Gelest Product Code No. DMS-D-56, DMS-T62, DMS-T61, DMS-D72.

Conventional catalysts may be used in the coatings useful in the practice of the present invention. The catalysts include platinum and platinum compounds, such as Ashby catalyst and other known to these skilled in the art. One example of a highly active platinum catalyst (the "Karstedt catalyst") is disclosed in U.S. Pat. No. 3,775,452, which is incorporated by reference. Vinyl-terminated polydimethylsiloxane can react with a polymethylhydrosiloxane cross-linker in less than one minute at ambient temperature with as little as 10 ppm of the Karstedt catalyst. Novel fast curing platinum catalysts have been developed to improve upon the characteristics of the Karstedt catalyst and other catalysts. An example of such a catalyst is a catalyst prepared by reacting the Karstedt catalyst with ethynylcyclohexanol (as disclosed in U.S. patent application Ser. No. 13/296,771) Such a catalyst provides greater control over curing of silicone coating solutions. This is conventionally referred to as "command cure".

The formula of the resulting platinum complex catalyst (platinum ivinyltetramethyldisiloxane ethynylcyclohexanol complex) is:

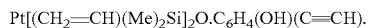

$Pt[(CH_2=CH)(Me)_2Si]_2O.C_6H_4(OH)(C=CH)$.

Such a preferred command cure catalyst is inhibited at low or ambient temperatures and activated at higher or curing temperatures, that is, the catalyst is inactivated at lower or ambient temperatures and activated at higher or curing temperatures. This allows for command cure (command cure catalytic action) of the cross-linkable components in silicone coatings to rapidly form coating films at desired curing temperatures, and provides for long pot life.

The silicone coating solutions that are used in the coating processes of the present invention to coat surgical needles may be prepared in the following manner. The above-described silicone polymers and platinum catalysts, including the novel platinum complex catalyst, are dispersed into organic solvents to form the novel lubricious coating solutions or compositions of the present invention. Both aromatic and aliphatic solvents can be used for the silicone dispersions, however, aromatic solvents are most commonly used for silicone dispersions. Typical examples of useful aromatic solvents include, but are not limited to, xylene and toluene. Aliphatic solvents which are useful include, but are not limited to, pentane, heptanes, hexane and their mixtures. An example of an aliphatic solvent mixture is Exxon Isopar K® solvent. The organic solvents are added at a concentration sufficient to provide effective blending of the silicone polymer components into a homogeneous coating solution that may effectively applied by conventional coating process equipment. The total solvent concentration sufficient to be effective is typically between about 75 wt. % to about 99.5 wt. %, and is more typically between about 85 wt. % to about 98.5 wt. %, depending upon the coating thickness requirement. Those skilled in the art will appreciate that the coating thickness can be engineered by changing the solids content of the coating solution.

The following procedure as described utilizes conventional mixing equipment in typical and conventional production facilities. The coating compositions useful in practice of the processes of the present invention may be preferably prepared in the following manner. Initially, a suitable organic solvent such as xylene is added to a conventional mixing vessel together with a suitable platinum catalyst and mixed for a sufficiently effective time, for example, up to about 10 minutes, to form a solution. Then, a suitable non-cross-linkable silicone polymer component such as trimethylsilyl-terminated polydimethylsiloxane and a suitable vinyl-terminated cross-linkable silicone polymer component such as polydimethylsiloxane are dispersed into the solution for a sufficiently effective time; for example, for up to about two hours until fully homogeneous. A suitable organic solvent such as Isopar K® solvent is then added to the solution, and the solution is further mixed for a sufficiently effective time, for example, for about one hour prior to the addition of a suitable cross-linking agent such as polymethylhydrosiloxane cross-linker. Then, the cross-linking agent is added to the solution and the solution is fully blended for a sufficiently effective time. The length of such time can be, for example, one additional hour after all of the components have been added to the mixing vessel.

Other conventional blending and mixing processes and equipment may be used to manufacture the novel silicone coating compositions of the present invention. For example, the sequence can be modified to some extent when using various other suitably effective conventional mixing equipment, such as a double planetary mixer. All of the components may be mixed in one step in such equipment.

Although not necessarily preferred, in order to reduce VOC emissions, it is possible to formulate the lubricious silicone coating compositions in a less volatile organic solvent, an aqueous/organic solvent mixture, or an aqueous solvent solution. This can be done by done in a conventional manner similar to that used for conventional low VOC or water-based polymeric coatings.

In the following paragraph the wt. % is the wt. % of total solid content in the coating solution. The coating compositions useful in the coating processes of the present invention will contain sufficient amounts of the polymeric components, cross-linking agent, catalyst, and solvent to effectively provide a silicone coating having high lubricity and durability, a long pot life, and be suitable for application in conventional coating processes using conventional coating equipment. Typically, the amount of the non-cross-linkable silicone polymer will be about 10 wt. % to about 90 wt. % (total solids), more typically about 30 wt. % to about 70 wt. % (total solids), and preferably about 40 wt. % to about 60 wt. % (total solids). The amount of the cross-linkable silicone polymer will typically be about 10 wt. % to about 90 wt. % (total solids), more typically about 30 wt. % to about 70 wt. % (total solids), and preferably about 40 wt. % to about 60 wt. % (total solids). The amount of the silicone cross-linking agent will typically be about 0.2 wt. % to about 1.8 wt. % (total solids), more typically about 0.6 wt. % to about 1.4 wt. % (total solids), and preferably about 0.8 wt. % to about 1.2 wt. % (total solids). The amount of the platinum catalyst based upon the total solids in the lubricious silicone coating compositions (platinum element in total solids) will typically be about 0.0004 wt. % to about 0.0036 wt. %, more typically about 0.0012 wt. % to about 0.0028 wt. %, and preferably about 0.0016 wt. % to about 0.0024 wt. %.

The amount of organic solvent in the coating compositions useful in the novel coating processes of the present invention will typically be about 75 wt. % to about 99.5 wt. %, more typically about 28 wt. % to about 99 wt. %, and preferably about 15 wt. % to about 98.5 wt. %. Those skilled in the art will appreciate that the amount of solvent present in the coating compositions will vary with several factors, and that the solvent quantity in the coating compositions will be selected to engineer an efficacious coating. The factors typically considered include the method of application, the method of cure, the coating equipment utilized, ambient conditions, thickness, etc. It will be appreciated that each of the components of the coating compositions of the present invention may consist of blends of those components. For example, two or more different molecular weight non-cross-linkable silicone polymers may be used, or two or more cross-linkable silicone polymers having different functionalities and/or molecular weights may be used, etc.

The silicone lubricious coating compositions used in the processes of the present invention may be applied to one or more surfaces of a medical device, such as a surgical needle, using conventional coating techniques and processes and conventional coating equipment. One example of coating equipment that can be used to apply the coatings includes, but is not limited to, simple dip coating tanks and in-line convection ovens for curing. The coating compositions can also be applied by conventional brushing, rolling, or spraying processes, and any equivalent processes, and may be cured as well by any equivalent curing methods.

The novel coating processes of the present invention have particular applicability for applying silicone coatings to surgical needles in automated, high speed production processes.

In a conventional automated system, the surgical needles are mounted to a conventional carrier strip or other mechanical carrier and moved to a piece of conventional coating process equipment for application of the silicone coating, for example, into a conventional dip tank containing a silicone coating composition, although other conventional application methods and equipment may be used. The needles reside in the dip tank for a sufficient period of time to assure that the entire surface of each needle is effectively wetted and coated with the silicone coating solution. The coated needles are then moved from the coating tank (or other application process equipment) to a blow-off station. In the processes of the present invention, in the blow-off station, a stream of air or other gas is directed at each needle in a direction substantially in alignment with the central major axis of the distal section of the needle. The air stream is preferably a pressurized stream of compressed air emitted from a conventional gas nozzle. The needle remains in the air stream for a sufficient period of time to effectively move silicone on the needle body up to the distal needle end and distal piercing tip. Depending upon the needle size and configuration, and the type of silicone coating solution utilized, the residence time in the air stream may typically vary, for example, from about 0.5 seconds to about 1 second; preferably, the residence time in the air stream will be about 1 second to about 5 seconds. If desired, the direction of the air stream may vary with regard to the central major axis of the distal end of the needle by about +/−20°. Optionally, an initial or first air or gas stream may be directed at the needle in the blow-off station prior to the coated needle being subjected to the final air stream that is directed in substantial alignment with the central major axis of the distal end of the needle. The optional air stream will be directed such that it is preferably parallel to the direction of the movement of the needle. The direction of the optional stream may optionally range from −20° to +20°, with respect to the horizontal direction of the needle carrier strip and parallel to the direction of strip movement. Preferably, the direction of the optional gas stream is from zero to about 20° upwards with respect to the horizontal direction of the needle carrier strip and parallel to the direction of the strip movement. The optional air stream step is provided to provide additional movement of the silicone coating.

The gas or air stream will have sufficiently effective parameters to provide the desired coating movement, removal, and other requirements. For example, the gas pressure will be about 5 psi to about 60 psi, more typically about 10 psi to about 40 psi, and preferably about 15 psi to about 30 psi. The distance of the needle from the exit orifice of the gas nozzle will, for example, be about 2 mm to about 20 mm, more typically about 4 mm to about 15 mm, and preferably about 6 mm to about 10 mm. The gas volume from the nozzle will, for example, typically be about 30 L/min to about 150 L/min, more typically about 50 L/min to about 120 L/min, and preferably about 75 L/min to about 95 L/min. The gas or air stream flow velocity will sufficiently effective to provide the desired movement of the uncured coating solution on the needle; for example, typically about 25 m/min to about 1,000 m/min, more typically about 50 m/min to about 750 m/min, and preferably about 100 m/min to about 500 m/min. It will be appreciated that these parameters may vary depending upon several factors, such as the coating chemistry, the application process, production speeds, needle size, atmospheric variables, ambient air variables, etc.

The coated needles are then moved to a conventional curing apparatus in line by passing the coated device through a conventional drying oven for a sufficiently effective time. The curing times will vary; for example, from 5 seconds to about one hour, and will vary with respect to parameters such as the cross linker concentration, catalyst concentration, coating thickness, ambient conditions, device construction and material type, etc. However, the cure times can be as short as about 30 seconds at 300° C., 20 seconds at 450° C., or about 6 seconds at 600° C. Flashcure (i.e., instantaneous or rapid cure) can also be achieved.

Referring to FIG. 1, a schematic of surgical needles 10 mounted to a carrier strip 50 is shown. The needles 10 are seen to have curved needle bodies 15, and distal piercing points 17. The needles 10 are also seen to have proximal ends 20 and tail members 25 extending from proximal ends 20. The tail members 25 are cut from the needles 10 during the final stages of the manufacturing process when the needles 10 are removed from the strip 50 to form the finished surgical needles. The tail members 25 are used to mount the needles 10 to the strips 50 during the manufacturing process. The strips 50 are seen to be conventional needle mounting strips that are used in high speed manufacturing processes to transport needles 10 to and from various process stages, e.g., cutting, grinding, coating, etc. The strips 50 are seen to have conventional pilot holes 55 for engagement with conventional material movement equipment to translate or move the strip 50 and needles 10 through the manufacturing process and to various process equipment and processing stages. Strip 50 is also seen to have mounting tabs 60 that engage the tail members 25 of needles 10.

Figure 2:
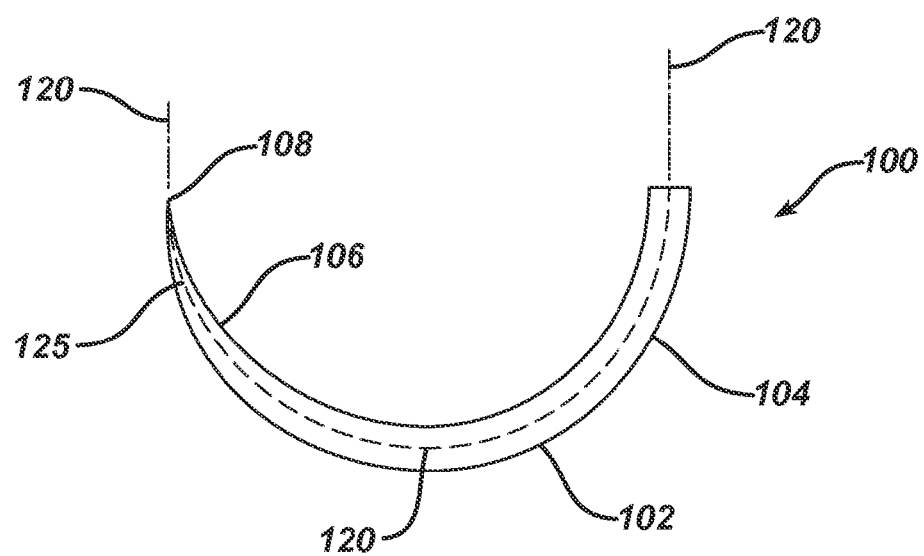
FIG. 2 is a schematic of a typical curved surgical needle having a longitudinal central axis and a distal section with a piercing point.

Referring to FIG. 2, an illustration of a typical curved surgical needle 100 is seen having a longitudinal central axis 120 and a distal section 106 with a piercing point 108. The needle is seen to have a curved configuration. The needle has a needle body 102 and a proximal section 104. The longitudinal central axis 120 follows the contour of the needle 100 and is seen to have a distal segment 125 associated with distal section 106 of needle 100.

Figure 3B:
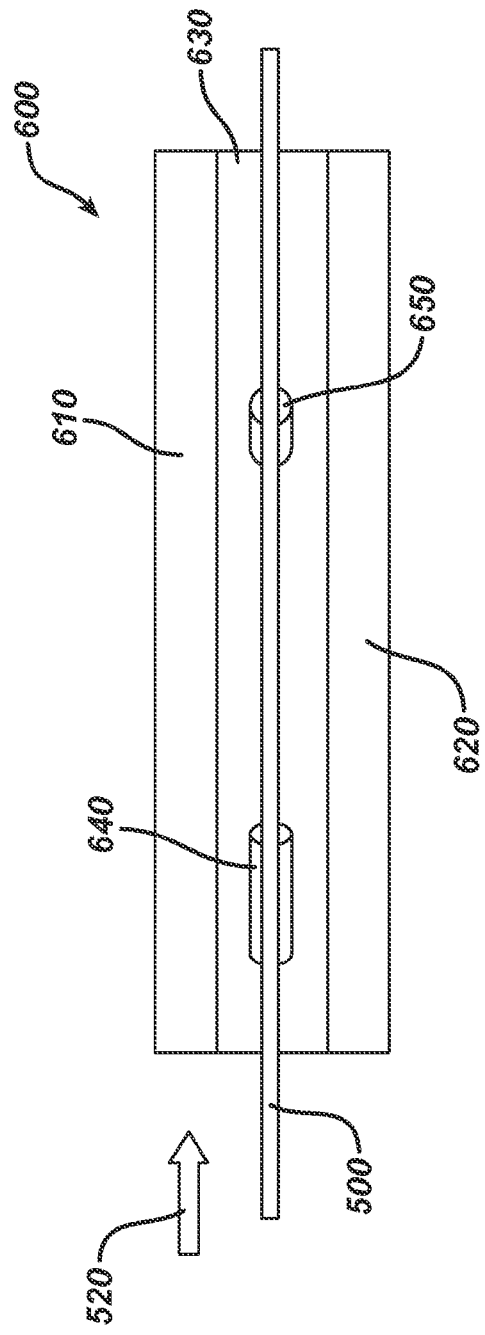

The inventive coating system of the present invention is schematically shown in FIGS. 3A-E. FIG. 3A shows a needle carrier strip 500 with surgical needles 510 mounted on the strip 500. Arrow 520 indicates the direction of the movement of the needle strip 500. The arrows 530 a, b, c indicate the direction of the air or gas from an optional first air blowing nozzle. The direction of air will range from substantially aligned with the direction of the horizontal movement of the needle strip to tilted upwards from horizontal, with an upward tilt of from about zero degrees to a few degrees less than the full alignment with longitudinal central axis 540 of the distal tip section 548 of the needle 540 adjacent to needle tip 545, such as 10-50 degrees off full alignment with longitudinal central axis of the distal tip section 548 of the needle 510 having needle tip 545, such as 10-50 degrees off full alignment with longitudinal central axis 540 of the distal tip section 548. In one embodiment, the direction of the air from the optional first air blowing nozzle is horizontal. In another embodiment, the direction of the air from the optional first air blowing nozzle is 10-20 degrees upwards from horizontal. In yet another embodiment, the direction of the air from the optional first air blowing nozzle is about 30 degrees lower than longitudinal central axis of the distal tip section 548 of the needle 540.

Arrow 550 indicates the direction of air from the main air blowing nozzle of the process of the present invention. The directionality of the air from the main air blowing nozzle is in substantial alignment with the longitudinal central axis 540 of the distal tip section 548 of the needle 510, such as when the angle between the direction of the air 550 from the main air blowing nozzle and the longitudinal central axis 540 of the distal tip section 548 of the needle 510 is from zero degrees to about +/−20 degrees, for example such as +10 degrees or −10 degrees.

FIGS. 3B and 3C show a trough 600 used in the process of the present invention formed by walls 610 and 620 mounted on a base 630, with needle carrier strip 500 and needles 510 passing between walls 610 and 620, and, above base 630 in the direction indicated by arrow 520, immediately after coating of needles 510 with a silicone coating solution. FIG. 3B is a top view of trough 600 and FIG. 3C is a side view of trough 600 with a partial cutout of wall 620. Optional first air blowing nozzle 640 and main air blowing nozzle 650 are shown directing air flow towards needles 510 mounted on carrier strip 500, with optional first air blowing nozzle 640 substantially aligned with the carrier strip direction of movement 520 or tilted upwards from the carrier strip direction of movement 520 as shown in FIG. 3C and main air blowing nozzle 650 substantially aligned with the longitudinal central axis 540 of the distal tip section 548 of the needle tip 545.

Referring now to FIG. 3D, a schematic of air blowing effects on uncured coating droplets is shown with needles 510 at successive positions in the process. Position 1 shows coating solution droplet 700 forming on needle 510 after dip coating or spray coating; Position 2 shows coating droplet 700 moving towards needle tip 545 driven by air flow 530 from optional first air blowing nozzle 640; and, Position 3 shows coating droplet 700 moving further towards the needle tip 545 and covering needle tip 545, driven by air flow 550 from main air blowing nozzle 650 aligned with section 548.

Figure 3E:
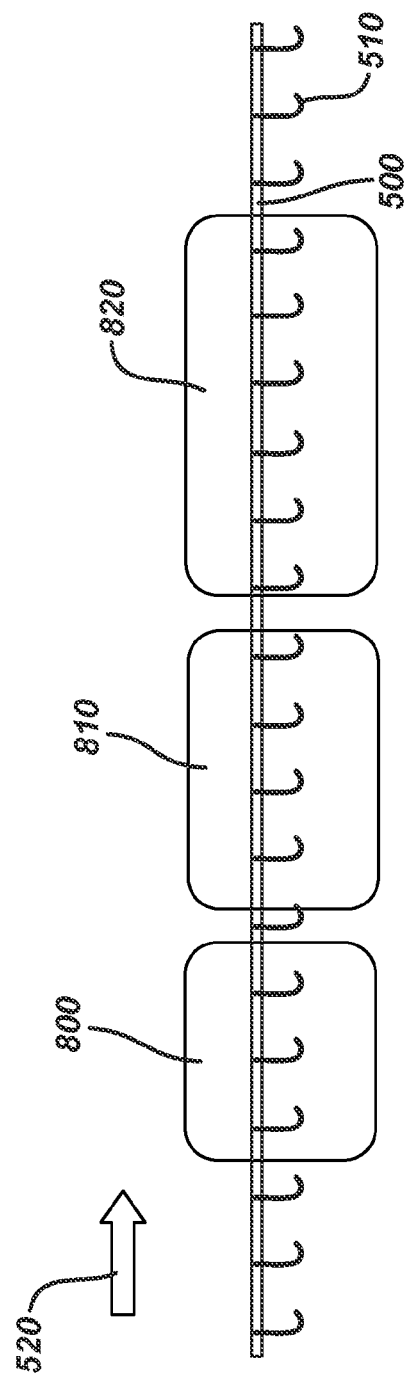

Referring now to FIG. 3E, a schematic of the needle processing of the present invention is shown, with carrier strip 500 moving in the direction 520 with needles 510 mounted on the carrier strip 500. As shown in FIG. 3E, needles 510 pass though (i) silicone solution coating chamber 800, followed by (ii) blow-off chamber 810, substantially comprising (not shown) trough 600 with optional first air blowing nozzle and main air blowing nozzle directing air flow towards needles 510 mounted on strip 500; followed by (iii) heat tunnel chamber 820.

Preferably, there is a very short time elapsing between treatments in each chamber, with this time being a function of the speed of the needle carrier 500 and the distance between chambers 800, 810, 820. In various embodiments, the time between needles exiting coating chamber 800 and entering blow-off chamber 810 is, for example, from about 0.01 seconds to about 10 seconds, such as 0.2 seconds, 0.5 seconds, or 3 seconds. In various embodiments, the time between needles exiting blow-off chamber 810 and entering heat tunnel 820 is, for example, from about 0.01 seconds to about 3 seconds, such as about 0.2 seconds or about 0.5 seconds.

Other conventional curing techniques which can be utilized with the novel silicone coating compositions of the present invention include thermal (e.g., convection heating), ultraviolet light, plasma, microwave radiation, electromagnetic coupling, ionizing radiation, laser, and the like. Prior to coating, the surfaces of the medical devices will be prepared in a conventional manner using conventional processes such as electro-polishing, oxidation, ultrasonic cleaning, plasma etch, chemical cleaning, and the like.

Other conventional coating application processes and equipment may be used in the practice of the novel invention of the present invention including spray guns, brushes, ultrasonic assisted spray, as well as any other coating application methods known to these skilled in the art, and the like.

Coating performance for medical devices can be tested with a variety of friction or adhesion tests. In the case of surgical needles, coating performance and integrity is evaluated using a conventional penetration testing device known as an ECNT (curved needle tester). A coated surgical needle is mounted to the test apparatus and held using self-locking tweezers or a similar holding device. The coated needle is then passed through a medium that is representative of general human tissue. Approximately half of the needle length is passed through the medium and then retracted prior to the next pass. The test media is typically a type of synthetic polymer or rubber that is representative of mammalian tissue (for example, Duraflex™, manufactured by Monmouth Rubber and Plastic Corporation, Monmouth, N.J.). A typical test includes using a batch of 10 needles that are individually passed through the media 30 times each. The maximum force is recorded for each pass and used as a measure of the coating performance. Typically the penetration force increases with each successive pass as the coating wears off from the needle. Further details of the equipment and method can also be found in U.S. Pat. No. 5,181,416, which is incorporated by reference.

The following examples are illustrative of the principles and practice of the present invention although not limited thereto. The examples are illustrative of the outcomes of penetration testing performance of surgical needles which were made according to the present invention.

EXAMPLE 1

Ethicon RB-1 surgical needles (16 mil diameter, no suture attached) were coated with a mixture of the silicone components summarized in Table 1. The coating was applied as described in the subsequent examples.

TABLE 1

| Coating Formulation | | |
| --- | --- | --- |
| Component | Trade Name | Weight (g) |
| Trimethylsilyl terminated polydimethysiloxane | Gelest DMS T72 | 960 |
| dimethylvinyl silyl terminated polydimethysiloxane | Gelest DMS V52 | 960 |
| Platinum catalyst 0.02% solution | | 384 |
| Trimethylsilyl terminated polymethylhydrosiloxane | Gelest DMS HMS 991 | 19.2 |
| Solvent 1 | Xylene | 4269.1 |
| Solvent 2 | Exxon Isopar K | 9408 |

EXAMPLE 2

Effect of Additional Oven Cure

RB-1 needles were dipped into the mixture of silicones solution summarized in Table 1 (referred to as new silicone herein after) in a dip tank. The excess coating solution on the needles had been removed using the novel process of the present invention as illustrated in FIG. 3. The pressure on the blow off device was set at 10 psi. The new silicone coated needles (Batch 2A) were heated at 650° F. for 40 seconds in a heat tunnel comprising a heated tube as known in the art (i.e., flash cured in a heated tunnel). The heat tunnel was of a tubular shape and equipped with a Leister Hotwind hot air blower (manufactured by Leister Technologies AG, Kaegiswil, Switzerland). Half of the coated needles were submitted for penetration test, and other half of the needles were cured further by exposing to 195° C. for 120 minutes in a convection oven (Batch 2B). Penetration testing was performed on these two sets of needles as described in the testing section. The results are from penetration testing done using 10 individual needles. The coated needles were penetrated 30 times each. The average penetration force for each pass is summarized in Table 2A.

TABLE 2A

| Needle Penetration Test: Example 2 | | |
| --- | --- | --- |
| Penetration# | Avg. Force (g) Batch 2A(Flash cured) | Avg. Force (g) Batch 2B (2 hr cured) |
| 1 | 30.3 | 33.5 |
| 10 | 42.0 | 41.0 |
| 20 | 50.2 | 48.4 |
| 30 | 58.8 | 53.6 |

There were minor differences in penetration performance after the additional 2 hour oven cure. The silicone coating largely achieves its lubrication performance with the in-line flash cure process only.

Effect of Pressure of the Air Blowing Nozzle

The effect of the air pressure was also studied. The pressure on the air blowing nozzle was set at 10, 15, 20, 25 and 35 psi. The silicone coated needles were heated at 650° F. for 40 seconds and cured further in a convection oven at 195° C. for 120 minutes. Penetration testing was done using 10 individual needles. The coated needles were penetrated 30 times each. The average penetration force for each pass is summarized in Table 2B.

TABLE 2B

| Needle Penetration Test: Example 2 (Effect of Different Blow-Off Pressure) | | | | | |
| --- | --- | --- | --- | --- | --- |
| Penetration# | Avg. Force (g) Batch 2B (10 psi) | Avg. Force (g) Batch 2C (15 psi) | Avg. Force (g) Batch 2D (20 psi) | Avg. Force (g) Batch 2E (25 psi) | Avg. Force (g) Batch 2F (35 psi) |
| 1 | 33.5 | 33.3 | 32.7 | 35.8 | 30.6 |
| 10 | 41.0 | 42.2 | 39.7 | 44.2 | 50.0 |
| 20 | 48.4 | 45.3 | 44.8 | 50.3 | 61.8 |
| 30 | 53.6 | 49.1 | 50.1 | 54.0 | 68.8 |

It was observed that 15 and 20 psi blow-off pressures gave the lowest penetration performance from this study.

Effect of Blow-Off Angle, Comparison to Conventional Blow-Off Angle

The effect of the angle of the blow-off air stream was also investigated.

The comparison Batch 2G was prepared as follows. RB-1 needles were dipped into the mixture of silicones in solution summarized in Table 1 in a dip tank. The excess coating solution on the needles had been removed using a conventional blow-off air stream, wherein the air stream was directed in a direction parallel to the direction of the carrier strip movement immediately after removal from the dip tank. The gas pressure to the blow-off device was set at 20 psi. The new silicone coated needles (Batch 2G) were heated at 650° F. for 40 seconds in a heated tunnel as described above and cured further by exposing to 195° C. for 120 minutes at a convection oven. Penetration testing was performed on the needles as described above. The results were from penetration testing done using 10 individual needles. The coated needles having cured coatings were penetrated 30 times each. The average penetration force for each pass is summarized in Table 2C.

The ECNT (curved needle test) results on the silicone coated RB-1 needles using the process of the present invention (Batch 2D) at 20 psi air pressure is also listed in Table 2C for the purpose of comparison.

A set of Nusil 4162 coated RB-1 needles (Batch 2H) using a conventional process, wherein the blowoff direction was parallel to the direction of needle movement on the carrier strip, were tested as the control sample and the results are also included in Table 2.

TABLE 2C

Needle Penetration Test: Example 2 (Effect of Blow-Off Angle)

| Penetration# | Avg. Force (g) (New Coating/New Blow Off Unit) Batch 2D | Avg. Force (g) (New Coating/Old Blow Off Unit) Batch 2G | Avg. Force (g) Batch 2H |
|---|---|---|---|
| 1 | 32.7 | 29.9 | 38.0 |
| 10 | 39.7 | 46.3 | 73.4 |
| 20 | 44.8 | 56.2 | 87.1 |
| 30 | 50.1 | 63.4 | 93.0 |

The needles coated using the process of the present invention gave substantially lower penetration forces in $10^{th}$, $20^{th}$ and $30^{th}$ pass, compared to a conventional blow-off unit, on exactly same type of silicone coating at the same blow off pressure. The new process/new coating leads to 50% reduction on $20^{th}$ pass, comparing to the current product.

Raman Investigation of Coating Batches 2D and 2G

Figure 4:
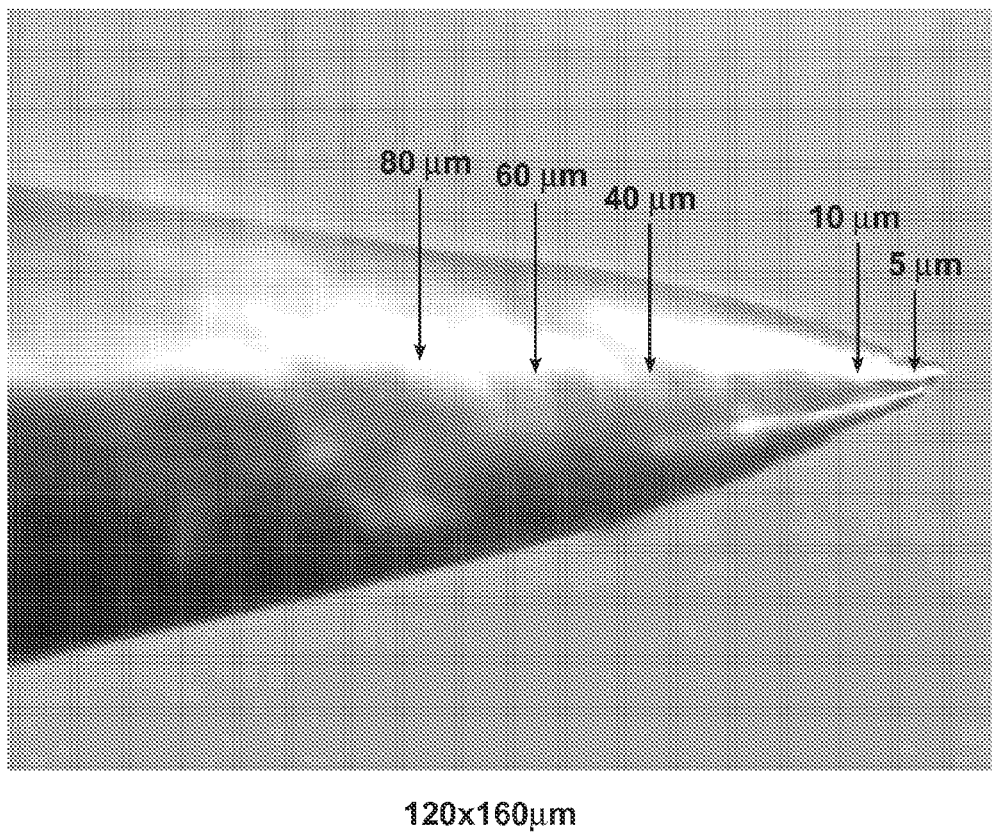
FIG. 4 is a photograph of a magnified section of the tip of a needle of Batch 2G coated in accordance with Example 2.

Conventional Confocal Raman Microscopy was used to investigate the presence of silicone coating around the tip geometry of the three types of needles listed in Table 2C. The Raman spectra were collect at 10 um away from the tip at the wave length of 1410 cm-1 as illustrated in FIG. 4. The absorption band corresponds to the CH species, which indicates the presence of silicone at this particular spot.

Figure 5:
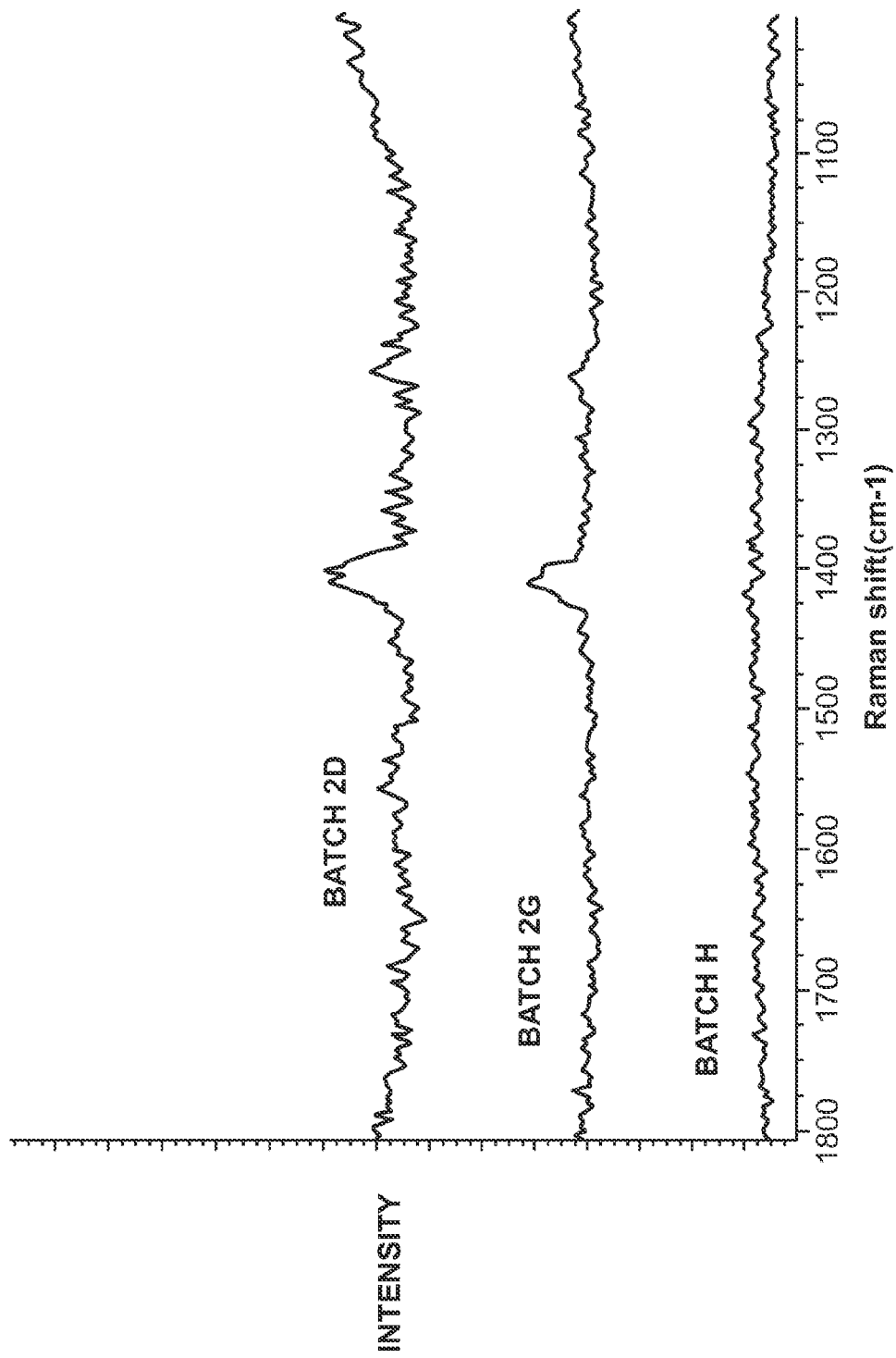
FIG. 5 is a graph of Raman Spectra of the coated needles of Batch 2D and Batch 2G of Example 2 compared with the coated needles of Batch H; intensity is in arbitrary units.

The Raman spectra at 10 um of these three needles are shown in FIG. 5.

The needle with a coating coated with the process of the present invention had more silicone on its tip geometry post-cure as compared to the needle coated with the prior art process using a conventional type of blow-off device. There was no silicone present on the tip of a needle coated with Nusil 4162 using the prior art process. The nearest spot to the tip with silicone coverage was 150 um away from the tip from the confocal Raman analysis.

EXAMPLE 3

Ethicon RB-1 needles were dipped into the mixture of silicones solution summarized in Table 1 in a conventional dip tank. The excess coating solution on the needle was removed in accordance with the process of the present invention using the blow-off device illustrated in FIG. 3. The coated needles were heated at 810° F. for 20 seconds (in a heated tunnel as described above) and cured further by exposing to 195° C. for 120 minutes in a conventional convection oven. Penetration testing was performed on these two sets of needles as described in the testing section. The results are from penetration testing done using 10 individual needles. The coated needles were penetrated 50 times each. The average penetration force for each pass is summarized in Table 3.

TABLE 3

Needle Penetration Test: Example 3

| Penetration# | Avg. Force (g) |
|---|---|
| 1 | 62.4 |
| 10 | 56.0 |
| 20 | 53.3 |
| 30 | 56.4 |
| 50 | 57.0 |

The penetration forces did not reduce after 50 passes through synthetic media.

EXAMPLE 4

The coating process of the present invention was performed twice, with dip coating, blow-off, curing followed by a second dip coating, blow-off, and curing as follows. Ethicon RB-1 needles were dipped into the mixture of silicones in solution summarized in Table 1 in a dip tank. The excess coating solution on the needles had been removed in accordance with the process of the present invention using a blow-off device illustrated schematically in FIG. 3. The coated needles were heated at 810° F. for 20 seconds in the heating tunnel described above and dipped again in the silicone coating solution outlined as Example 1 in Table 1. The excess solution on the needles was removed once more in accordance with the process of the present invention by the blow-off device, the coated needles were heated to 520° F. for 20 seconds in the heating tunnel described above and cured further by exposing to 195° C. for 120 minutes in a conventional convection oven. Penetration testing was performed on these two sets of needles as described in the testing section. The results are from penetration testing done using 10 individual needles. The coated needles were penetrated 30 times each. The average penetration force for each pass is summarized in Table 4.

TABLE 4

Needle Penetration Test: Example 4

| Penetration# | Avg. Force (g) (2 hr cured) |
|---|---|
| 1 | 28.2 |
| 10 | 39.1 |
| 20 | 44.3 |
| 30 | 47.7 |

As described above, this Example demonstrated application of the inventive process for a double coat of the needles with silicone coating.

Although this invention has been shown and described with respect to detailed embodiments thereof, it will be understood by those skilled in the art that various changes in form and detail thereof may be made without departing from the spirit and scope of the claimed invention.

We claim:

1. A method for coating surgical needles, comprising:
applying a silicone coating to a curved surgical needle having a longitudinal central axis and a distal tip section and a distal tip, wherein the needle is mounted to a carrier, by dipping the surgical needle into a silicone coating solution by moving the needle into a silicone coating solution bath, wherein the needle is mounted to the carrier such that the tip of the needle is pointing up;
moving the needle out of the coating bath;
directing a stream consisting essentially of a gas to the needle along a path that is in a direction substantially parallel to the longitudinal central axis of the distal tip section of the needle, said stream directed distally toward the distal tip, to remove excess coating solution from the needle, and moving at least some of the coating to the tip section while retaining sufficient silicone coating solution on the tip; and,
curing the silicone coating, wherein said needle has improved penetration performance.

2. The method of claim 1, wherein the coating is flash cured.

3. The method of claim 1, wherein the coating is cured by a platinum catalyst within one minute at elevated temperature.

4. The method of claim 1, wherein the gas stream is angulated with respect to the longitudinal section of the distal tip section by about +/−20°.

5. The method of claim 1, wherein the needle is subjected to an initial gas stream directed at the needle in a direction different from the direction of the gas stream prior to the needle contacting the gas stream.

6. The method of claim 1, wherein the silicone coating solution comprises vinyl terminated polydimethylsiloxane, methyl terminated polymethylsiloxane, methyhydrosiloxane cross linker, platinum divinyltetramethyldisiloxane ethynylcyclohexanol complex and organic solvents.

7. The method of claim 1, wherein the carrier comprises a carrier strip.

8. A surgical needle, coated by the method of claim 1.

9. The method of claim 1, wherein the gas comprises air.

10. A method for coating surgical needles, comprising:
applying a silicone coating to a curved surgical needle having a longitudinal central axis and a distal tip section and a distal tip wherein the needle is mounted to a carrier, and wherein the needle is mounted to the carrier such that the tip of the needle is pointing up;
directing a stream consisting essentially of a gas to the needle along a path that is in a direction substantially parallel to the longitudinal central axis of the distal tip section of the needle said stream directed distally toward the distal tip, to remove excess coating solution from the needle, and moving at least some of the coating to the tip section, while retaining sufficient silicone coating solution on the tip; and,
curing the silicone coating, wherein said needle has improved penetration performance.

11. The method of claim 10, wherein the coating is flash cured.

12. The method of claim 10, wherein the coating is cured by a platinum catalyst within one minute at elevated temperature.

13. The method of claim 10, wherein the gas stream is angulated with respect to the longitudinal section of the distal tip section by about +/−20°.

14. The method of claim 10, wherein the needle is subjected to an initial gas stream directed at the needle in a direction different from the direction of the gas stream prior to the needle contacting the gas stream.

15. The method of claim 10, wherein the silicone coating solution comprises vinyl terminated polydimethylsiloxane, methyl terminated polymethylsiloxane, methyhydrosiloxane cross linker, platinum divinyltetramethyldisiloxane ethynylcyclohexanol complex and organic solvents.

16. The method of claim 10, wherein the coating is applied by a process selected from the group consisting of dipping, spraying, and brushing.

17. The method of claim 16, wherein the coating process is dipping in a coating bath tank.

18. The method of claim 10, wherein the carrier comprises a carrier strip.

19. A surgical needle, coated by the method of claim 10.

20. The method of claim 10, wherein the gas comprises air.

* * * * *